United States Patent [19]
Ivey et al.

[11] Patent Number: 5,985,336
[45] Date of Patent: *Nov. 16, 1999

[54] NUTRIENT FORMULATION AND PROCESS FOR FEEDING YOUNG POULTRY AND OTHER ANIMALS

[75] Inventors: Francis J. Ivey, Creve Coeur; Julia J. Dibner, Chesterfield; Christopher D. Knight, St. Louis, all of Mo.

[73] Assignee: Novus International, Inc., St. Louis, Mo.

[ * ] Notice: This patent is subject to a terminal disclaimer.

[21] Appl. No.: 08/647,719

[22] Filed: May 24, 1996

Related U.S. Application Data

[63] Continuation-in-part of application No. 08/597,815, Feb. 7, 1996, abandoned, which is a continuation-in-part of application No. 08/483,297, Jun. 7, 1995.

[51] Int. Cl.$^6$ ........................................................ A23K 1/18
[52] U.S. Cl. .................................. 426/2; 426/60; 426/623; 426/630; 426/635; 426/807; 426/573
[58] Field of Search .................................. 426/2, 807, 60, 426/623, 630, 635, 573

[56] References Cited

U.S. PATENT DOCUMENTS

| | | |
|---|---|---|
| 1,867,063 | 7/1932 | Dawe . |
| 2,620,274 | 12/1952 | Lewis et al. . |
| 2,946,722 | 7/1960 | Hoffman et al. . |
| 4,495,208 | 1/1985 | Friedman et al. ........................ 426/335 |
| 4,910,024 | 3/1990 | Pratt .............................................. 126/2 |
| 5,139,792 | 8/1992 | Ware et al. ................................... 426/2 |
| 5,514,408 | 5/1996 | Lan et al. .................................. 426/656 |
| 5,603,980 | 2/1997 | Bussiere et al. .......................... 426/641 |

FOREIGN PATENT DOCUMENTS

| | | |
|---|---|---|
| 1204057 | 5/1986 | Canada . |
| 0243548 | 11/1987 | European Pat. Off. ..... A61K 39/012 |
| 0287699A3 | 10/1988 | European Pat. Off. . |
| 0749695A1 | 12/1996 | European Pat. Off. . |
| 2031748 | 4/1980 | United Kingdom . |
| 2055034 | 2/1981 | United Kingdom . |
| WO 93/00017 | 1/1993 | WIPO . |
| WO 95/16461 | 6/1995 | WIPO . |
| WO 96/12413 | 5/1996 | WIPO ............................... A23J 1/04 |

OTHER PUBLICATIONS

"Cocci Control By Vaccine", From a talk by Dr. Eng Hong Lee at the 1991 Saskatchewan Poultry Industry Conference, Canada Poultryman, Sep. 1991, p. 39.

Gary Thornton "A Novel Cocci Vaccine System", Broiler Industry, May 1997, pp. 36, 38, 40.

Tadtiyanant, C., Lyons, J.J., Vandepopuliere, J.M., "Influence of Wet and Dry Feed on Laying Hens Under Heat Stress", Poultry Science, vol. 70, No. 1, (1991) pp. 44–52.

Thorne, D.H., Vandepopuliere, J.M. and Lyons, J.J., "Automated High Moisture Diet Feeding System for Laying Hens," Poultry Science vol. 68, No. 8, (1989), pp. 1114–1117.

"Immunocox Vaccine Immunogel Technical Manual", Wingo, Inc., P.O. Box 299, 18 N. Main St., Watkinsville, Georgia 30677, undated.

"HYDRO–PAK ", Midlantic Paper Products Inc., P.O. Box 8017 Greensboro, N.C. 27419, (910) 294–7172, undated.

Gib Taylor, "Ways to improve hatchability one percent, improve profits", *Poultry Digest*, Sep. 1995, pp. 20–21, 24, and 26.

*Primary Examiner*—Helen Pratt
*Attorney, Agent, or Firm*—Senniger, Powers, Leavitt & Roedel

[57] ABSTRACT

A nutrient formulation including moisture which is designed for use in poultry and other animals, and a method of feeding it which improves subsequent livability, cumulative feed efficiency and weight gain is disclosed. The method comprises making available for consumption ad libitum a high moisture material containing at least about 20% by weight water to the poultry or other animals before they are offered dry food ad libitum.

113 Claims, 2 Drawing Sheets

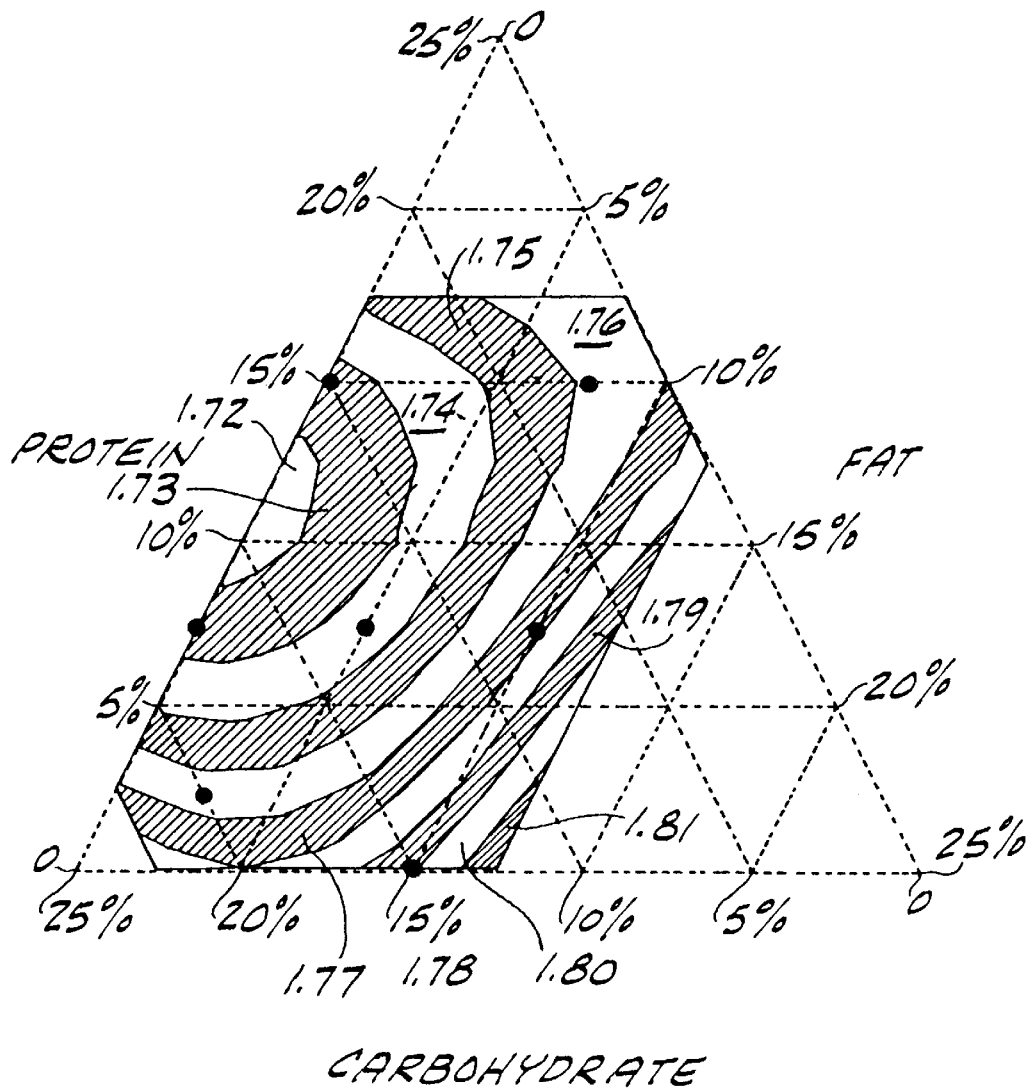

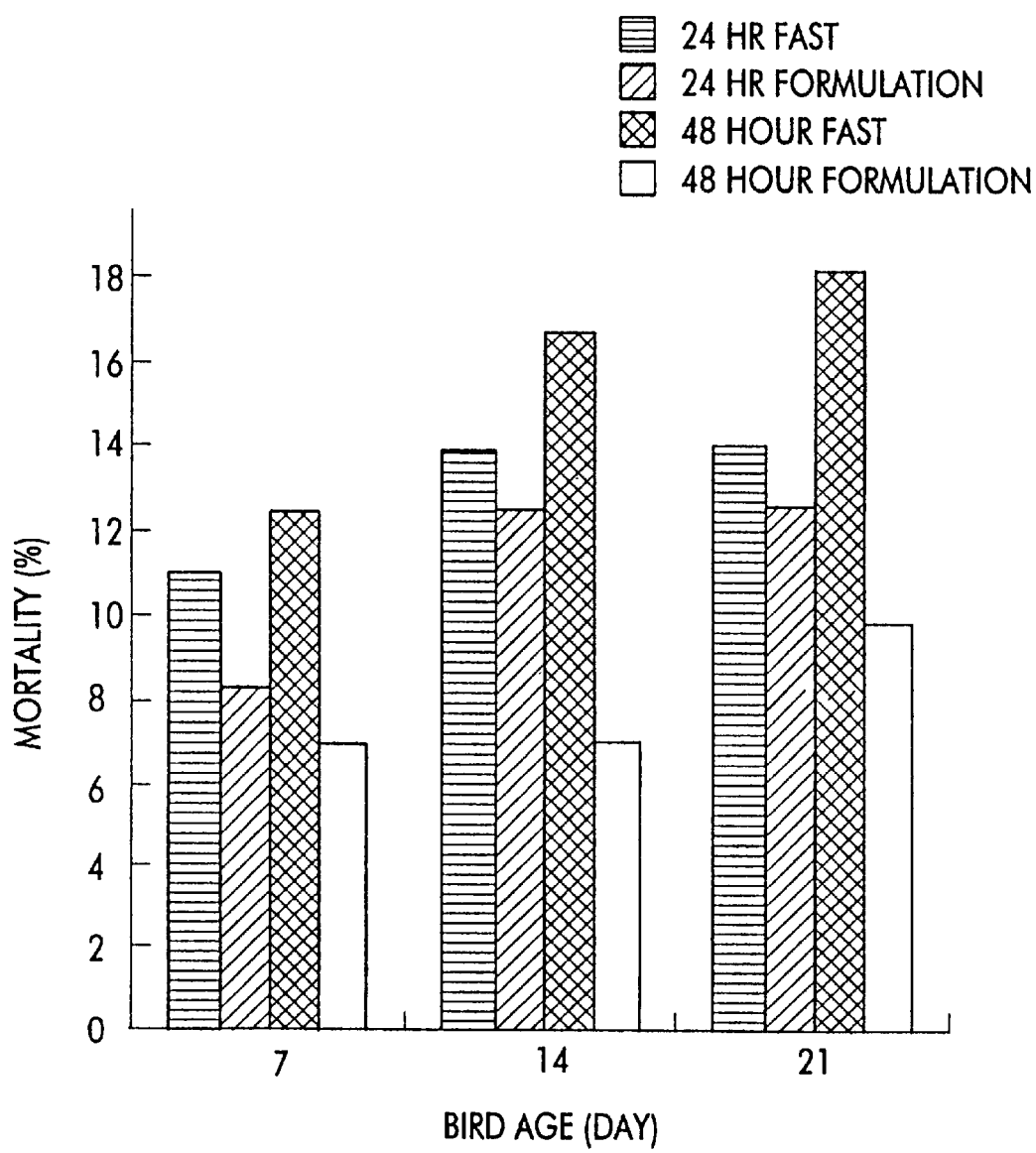

NUTRIENT FORMULATION AND PROCESS FOR FEEDING YOUNG POULTRY AND OTHER ANIMALS

This application is a continuation-in-part of application Ser. No. 08/597,815, now abandoned, filed Feb. 7, 1996 which is a continuation-in-part of U.S. application Ser. No. 08/483,297, filed Jun. 7, 1995, the entire contents of which are herein incorporated by reference.

BACKGROUND OF THE INVENTION

The present invention is directed to a high moisture material for providing nutrients, drugs, vitamins, minerals, bile salts, surfactants, probiotics, enzymes, peptides, hormones, prostaglandins, antioxidants, living cells, and immunoactive agents to poultry and other animals, and more particularly, a high moisture material and process which may be used to improve the health and enhance the livability, cumulative weight gain and feed conversion efficiency of poultry and other animals.

For economic reasons, the management of chick hatching in commercial facilities places high importance on percent chicks hatched of eggs set. To achieve hatch rates of 90%, early-hatching birds are often left in the hatch incubator for a period of time to allow the later-hatching chicks to emerge and dry. By the time the chicks are removed from the incubator tray, therefore, they will range in age from several hours up to about 2 days in age (as measured from hatching for each bird). This period is referred to as the post-hatch holding period.

After the chicks are removed from the incubator trays in a commercial hatchery, they are processed (inoculated and sexed) and then placed in boxes commonly referred to as chick boxes for shipping to the production farm. The processing period typically requires several hours and the chicks may reside in the chick boxes for several more hours before transit to the production farm actually begins.

Commercial hatcheries for poultry typically provide chicks for a number of production farms, often over a wide geographical area. Typically, feed and water are not provided until the birds reach the production farm and, as a result, the birds may go several days before feed and water are provided. The presence of the lipid-rich residual yolk sac and reserves of lipid in the liver, however, ensure that the minimal nutritional needs of hatchling birds are met (Freeman et al., *Development of the Avian Embryo*, London, Chapman and Hall, 1974). Thus, a period of inanition after hatching is normal in birds and does not necessarily threaten their survival (Entenman et al., *The Lipid Content of Blood, Liver, and Yolk Sac of the Newly Hatched Chick and the Changes That Occur in These Tissues During the First Month of Life*, J. Biol Chem., Vol. 133, pp. 231–241 (1940); Vanheel et al., *Resorption of Yolk Lipids by the Pigeon Embryo*, Comp. Biochem. Physiol., Vol. 68A pp. 641–646 (1981); Phelps et al., *The Posthatch Physiology of the Turkey Poult-III. Yolk Depletion and Serum Metabolites*, Comp. Biochem. Physiol., Vol. 87A, No. 2 pp. 409–415 (1987); Noble et al., *Lipid Changes in the Residual Yolk and Liver of the Chick Immediately after Hatching*, Biol Neonate, Vol. 56, pp. 228–236 (1989); Chamblee et al, *Yolk Sac Absorption and Initiation of Growth in Broilers*, Poultry Science, Vol. 72, pp. 1811–1816 (1992)). This does not mean, however, that using yolk residue as the single nutrient source in hatchlings will provide optimum subsequent livability, disease resistance, or gain and feed efficiency. The delayed placement has been shown to reduce subsequent livability (Kingston, *Some Hatchery Factors Involved in Early Chick Mortality*, Australian Veterinary Jour., Vol. 55, pp. 418–421 (1979); Fanguy et al., *Effect of Delayed Placement on Mortality and Growth Performance of Commercial Broilers*, Poultry Science, Vol. 59, pp. 1215–1220 (1980)), disease resistance (Wyatt et al., *Influence of Hatcher Holding Times on Several Physiological Parameters Associated With the Immune System of Chickens*, Poultry Science, Vol. 65, pp. 2156–2164 (1986); Casteel et al., *The Influence of Extended Posthatch Holding Time and Placement Density on Broiler Performance*, Poultry Science, Vol. 73, pp. 1679–1684 (1994)) and growth performance (Hager et al., *Education and Production Posthatch Incubation Time and Early Growth of Broiler Chickens*, Poultry Science, Vol. 62, pp. 247–254 (1983); Wyatt et al., *Influence of Egg Size, Eggshell Quality, and Posthatch Holding Time on Broiler Performance*, Poultry Science, Vol. 64, pp. 2049–2055 (1985); Pinchasov et al., *Comparison of Post-Hatch Holding Time and Subsequent Early Performance of Broiler Chicks and Turkey Poults*, British Poultry Science, Vol. 34, pp. 111–120 (1993)). Provision of individual nutrients such as glucose has not been found to consistently or permanently improve performance or livability when administered as a simple solution in the absence of other nutrients (Azahan et al., *Growth, Food Intake and Energy Balance of Layer and Broiler Chickens Offered Glucose in the Drinking Water and the Effect of Dietary Protein Content*, British Poultry Science, Vol. 30, pp. 907–917 (1989); Moran, *Effects of Posthatch Glucose on Poults Fed and Fasted During Yolk Sac Depletion*, Poultry Science, Vol. 68, pp. 1141–1147 (1989); Moran *Effects of Egg Weight, Glucose Administration at Hatch, and Delayed Access to Feed and Water on the Poult at 2 Weeks of Age*, Poultry Science, Vol. 69, pp. 1718–1723 (1990)).

Although provision of water and feed can result in performance superior to that of fasted, water-deprived birds, attempts to include water in the hatch incubator or in transport boxes have been unsuccessful. This is because humidity control and relatively high temperature are critical in ensuring high hatchability and because water alone or in a simple gruel can escape, resulting in some chicks getting wet. Chicks cannot regulate their body temperature sufficiently well to tolerate cooling by evaporation. Since inanition does not threaten survival, commercial practice is not to offer feed or water until the animals reach the farm.

SUMMARY OF THE INVENTION

Among the objects of the invention, therefore, may be noted the provision of a high moisture material to improve the health and enhance the livability, cumulative weight gain and feed conversion efficiency of poultry and other animals. The formulation may be fed, for example, immediately after hatching or birth of the animal and for this application, the formulation preferably excludes nutrients which are not used well during the first days of life and provides those which are readily used and confer a performance advantage. Also among the objects of the invention is a formulation which is stabilized against microbial growth, is resistant to synthesis and which can be packaged in bulk, shipped, extruded (with or without prior remixing of the bulk material) and divided into dosage unit form at the location of use of the formulation.

Briefly, therefore, the present invention is directed to a process for enhancing the health, livability, cumulative weight gain or feed conversion efficiency of poultry. The process comprises feeding the hatchlings a high moisture material before they are started on a diet comprising dry food. The hatchlings are fed the high moisture material beginning at a point in time preferably within the first 5 days of hatching, more preferably within the first 3 days of hatching.

The present invention is also directed to a composition and process for inoculating poultry and other animals with living cells such as yeast or bacteria. The animal is fed a high moisture material which contains a number of colony forming units of the cells which is sufficient to inoculate the animal and produce the desired effect.

The present invention is also directed to high moisture materials for enhancing the health, livability, cumulative weight gain or feed conversion efficiency of poultry. These high moisture materials contain at least about 50% by weight water, at least about 10% by weight digestible carbohydrate and, optionally, one or more additional ingredients selected from the group consisting of bile salts, surfactants, enzymes, enzyme co-factors, hormones, prostaglandins, peptides, immunoglobulins, cytokines, vaccines and other immunomodulators, antioxidants, amino acids, sources of amino acids and amino acid analogs, antibiotics, vitamins and minerals. The high moisture material is preferably prepared in bulk, extruded and divided into dosage unit form at the site where the high moisture material is fed to the animal.

Other objects and features of the invention will be in part apparent and in part pointed out hereinafter.

BRIEF DESCRIPTION OF THE DRAWINGS

FIG. 1 is a graph depicting the results of Example 12.

FIG. 2 is a bar graph depicting the results of Example 13.

DETAILED DESCRIPTION OF THE INVENTION

Surprisingly, it has been discovered that the growth of poultry can be stimulated, the livability, cumulative weight gain and feed conversion efficiency of the poultry can be improved by feeding to poultry a formulation of the present invention which is referred to herein as a high moisture material. As used herein, the term high moisture material means a colloid in which the dispersed phase (starch, gum or protein) has combined with the continuous phase (water) to produce a viscous, dough-like gel in which larger particles (e.g., particles greater than 5 $\mu$m in size) such as soy, corn or rice may be suspended.

In one embodiment of the present invention, the high moisture material is first fed to poultry hatchlings which are within five, four, three, two or even one day of hatching (as determined for each bird). Preferably, the high moisture material is fed to the hatchlings before they are offered dry food or allowed to drink water ad libitum, and more preferably before they are offered dry food, at all. The high moisture material may be placed, for example, in the hatching incubator along with the eggs from which the poultry will hatch so that the high moisture material is available to the hatchlings immediately upon hatching. Providing the high moisture material to the chicks prior to their introduction to solid food reduces the likelihood that the hatchlings will suffer by consuming dry food without simultaneously drinking.

In another embodiment of the present invention, the high moisture material may be made available to the hatchlings prior to or during shipping by placing the high moisture material in the chick boxes along with the chicks. In accordance with this embodiment, it is preferred that the high moisture material be placed in the chick boxes before transit begins so that the chicks will have the opportunity to consume the high moisture material before they begin travelling (that is, moving by surface or air transportation from the site of the incubator to a remote location such as a poultry production farm which may be, for example, one or more miles away from the location of the incubator). The amount of high moisture material placed in the chick boxes need not be sufficient to enable the chicks to feed on it for the entire transit period.

In a further embodiment of the present invention, the high moisture material is fed to the poultry after they are shipped from the site where they are hatched to a remote location such as a poultry production farm or other intermediate facility. After being shipped, some chicks do not readily begin eating dry food and drinking water when it is offered. For such applications, it may be desirable to feed the transported poultry the high moisture material until the poultry begin eating dry food and drinking water ad libitum. In addition, the high moisture material may also be fed to the poultry at this time or even a later time to administer drugs or other substances as described herein.

Typically, chick boxes are filled to capacity with hatchling chicks, leaving little additional room for the high moisture material of the present invention. As a practical matter, therefore, hatchling chicks which are in the chick boxes along with the high moisture material will stand upon, brush against, peck at, and otherwise come into contact with the high moisture material. Because hatchling chicks cannot regulate their body temperature sufficiently well to tolerate evaporative cooling, it is important that the hatchlings not be wetted by (or become damp from) the high moisture material under these conditions. Necessarily, therefore, the high moisture material should be resistant to synthesis under these conditions, that is, the high moisture material should not release an amount of water which is sufficient to wet the floor of the container in which the hatchlings are being held or the hatchlings as a consequence of their standing upon it, brushing up against it, pecking at it, or otherwise coming into contact with it.

When the high moisture material is initially offered to the poultry or other animal, it should contain at least about 40% by weight water (an amount which is in excess of the amount of water contained in "dry" poultry feeds), preferably at least about 50% by weight water, more preferably between about 50% and about 85% by weight water, and most preferably between about 60% and about 80% by weight water, based upon the weight of the high moisture material. The non-aqueous fraction of the high moisture material is sometimes referred to herein as the "dry matter" or the "solid matter" fraction, with the two terms being used interchangeably.

Carbohydrates provide a source of nutrition for the animals and, in addition, can aid in the formation of the solid. In general, digestible carbohydrates constitute at least about 8% by weight of the high moisture material, preferably at least about 10% by weight of the high moisture material and, for some applications, at least about 20% by weight of the high moisture material. The digestible carbohydrates contemplated herein include isolated carbohydrates such as corn starch, potato starch, wheat starch, rice starch, cellulose, pectin, agarose, and gums; bioavailable sugars such as glucose, fructose, and sucrose; chemically modified starches such as modified corn starch, methylcellulose, carboxymethylcellulose, and dextrin; humectants such as glycerol or propylene glycol; invert sugar; and ground complex carbohydrates such as corn, rice, oats, barley, wheat, sorghum, rye, millet, cassava, triticale and tapioca, in whole, ground, cracked, milled, rolled, extruded, pelleted, defatted, dehydrated, solvent extracted or other processed form. When included, modified starches preferably constitute at least about 0.01% by weight of the high moisture material.

The high moisture material is formed from a mixture of water and a combination of ingredients which enables the formation of a high moisture material from the mixture and which satisfies the nutrient specifications, if any. Depending upon the ingredients selected, preparation of the high moisture material may additionally require heating the mixture. In one embodiment, the mixture contains starch and is heated until the starch granules rupture and the mixture becomes viscous. See, for example, Lewis U.S. Pat. No. 2,593,577. In another embodiment, the high moisture material is formed from a colloidal solution containing a gum dissolved in water; some gums enable the formation of high moisture materials from the colloidal solution without heating whereas others require that the solution be heated to a temperature in excess of about 180° F. Generally, gums can constitute about 0.001% to about 5% by weight of the high moisture material. Gums which may be used for this purpose are generally high molecular weight molecules of plant or animal origin, usually with colloidal properties, which in appropriate solvents are able to produce gels, such as agar, algin and carrageenan derived from seaweeds, plant exudates such as gum arabic, ghatti and tragacanth, plant extracts such as pectin, plant seeds such as guar, locust bean, and animal exudates such as plasma, serum albumin, egg albumin, chitin and gelatin. Other gums include amylose and amylopectin and gums of bacterial origin.

See, for example, U.S. Pat. No. 5,217,740. In yet another embodiment, a gelatinizing aid such as carboxymethylcellulose, lignin, or a lignin derivative is dissolved in water to form a colloidal solution which forms a gel upon cooling.

After the ingredients of the high moisture material are mixed and heated (if necessary), the material may be allowed to form a gel in situ, transferred to another vessel or container for storage in bulk form, or cast in a shape and size which enables convenient feeding to animals. In a preferred embodiment, the mixture may be transferred to a container such as a drum or a deformable plastic which holds, for example, between about 25 and about 1,000 kilograms of the high moisture material.

For administration to poultry hatchlings, the gelled high moisture material preferably has a texture which enables the hatchlings to break the high moisture material apart by pecking; that is, the high moisture material is sufficiently soft such that the pecking of the hatchlings will cause the high moisture material to break or crumble into consumable fragments. Once broken into fragments, however, the high moisture material preferably does not adhere to the feathers or down of poultry hatchlings. In addition, it is preferred that the high moisture material comprise particles which are visible to the naked eye. Such particles include, for example, ground ingredients such as ground grains and seeds such as corn and soy beans, and other particles which do not exceed the size of a typical grain of white rice (i.e., about 1 mm).

Unless the high moisture material will be promptly fed to an animal, it is preferably stabilized against microbial growth. That is, upon being sealed and stored at room temperature for a period of at least about eight weeks the stabilized high moisture material will show no indication of microbial growth. The high moisture material may be stabilized, for example, by sterilizing, adding a microbial growth inhibitor such as methyl paraben or a sorbate thereto, or adjusting the pH of the mixture from which the high moisture material is formed. Preferably, the high moisture material is stabilized by adjusting the pH of the mixture with an acid to a pH within the range of about 3 to about 4, more preferably to a pH within the range of about 3 to 3.5. Such acid can be a low molecular weight carboxylic acid, preferably having a chain length of $C_2$–$C_{10}$, more preferably having a chain length of $C_2$–$C_7$, most preferably having a chain length of $C_2$–$C_5$. Examples of useful carboxylic acids include citric acid, propionic acid, and fumaric acid. Phosphoric acid can also be used. Propionic acid can be present in an amount of from about 0.5% to about 1% by weight of the present high moisture material; citric acid and fumaric acid can be present in an amount of from about 0.7% to about 2% by weight of the high moisture material.

The high moisture material may be fed to the animals in a variety of manners. For example, the amount required for feeding may be scooped, sliced or otherwise removed from the unit, container or vessel in which it is held and transferred to the animal(s) in unit form. To reduce labor, however, the unit doses of the solid may be generated from the bulk material by pumping or compressing the high moisture material and forcing it through an opening. The resulting material, referred to herein as an extrudate, is in the form of a high moisture material containing substantially the same amount of water as the bulk material. In one embodiment, the high moisture material may be in a compressible container which is compressed to force the high moisture material to flow through a die and to a location where it can be consumed by the animal(s). In some instances it may be preferred to combine the high moisture material with a heat labile or other ingredient before the high moisture material is fed to the animal(s); in these instances, the heat labile ingredient is added to the high moisture material at or near room temperature and the total mixture is then remixed before being divided into unit doses. Alternatively, the heat labile material may be sprayed onto the unit dose of high moisture material. In any event, however, the extrusion step should not cause the high moisture material to lose a significant amount of water or the desired texture. That is, the extrudate should preferably contain at least 40% by weight water, preferably at least about 50% by weight water, more preferably between about 50% and about 85% by weight water, and most preferably between about 60% and about 80% by weight water, based upon the weight of the extrudate and, in addition, the extrudate should be sufficiently soft such that the pecking of the hatchlings will cause the high moisture material to break or crumble into consumable fragments.

The high moisture material of the present invention resists synthesis when it contains at least about 5% protein. To increase its nutritional value for some applications such as longer-term feeding, the high moisture material preferably comprises at least about 7% by weight, more preferably at least about 10% by weight, of an amino acid source such as protein(s), amino acids, precursors or analogues of amino acids, and mixtures thereof. In addition, it is preferred that the weight ratio of all digestible carbohydrate to all amino acid sources in the high moisture material be between about 0.6:1 and 3:1, respectively. Exemplary amino acids are essential amino acids such as methionine, tryptophan, threonine, arginine and lysine. Exemplary amino acid precursors are 2-hydroxy-4-(methylthio)butanoic acid sold, for example, under the trademark Alimet® by Novus International (St. Louis, Mo.), and salts of 2-hydroxy-4-(methylthio)butanoic acid such as the calcium and sodium salts. Exemplary proteins include single cell proteins or hydrolysates of proteins such as those from yeast, algae or bacteria; isolated animal proteins, peptides or hydrolysates of proteins such as hemoglobin, myosin, plasma, or other serum proteins, collagen, casein, albumin or keratin; complex protein sources or hydrolysates of proteins such as milk, blood, whey, blood meal, meatmeal, feathermeal, fishmeal, meat and bone meal, poultry offal, poultry by-product meal, hatchery by-products, egg offal, egg white, egg yolk, and eggs without shells; plant protein or hydrolysate of proteins such as soybean meal,isolated soybean protein, wheat protein, wheat germ, distillers grains and gluten.

Although not preferred for certain applications, fat may also be included in the high moisture material in relatively small proportions. A suitable high moisture material, therefore, would comprise at least about 50% by weight water and no more than about 5% by weight fat, preferably no more than about 4% by weight fat. Suitable fats include fatty acids such as linoleic acid; isolated plant oils such as sunflower, safflower, soybean, peanut, canola, corn, rapeseed, olive, linseed and palmkernal; fat meals such as cottonseed, peanut, rapeseed, palmmeal and nut meals; and fats of animal origin such as egg yolk, lard, butter, poultry fat, tallow and fishoil.

The various processes disclosed herein can employ different types of high moisture materials depending upon the particular application. These high moisture materials can contain:

between about 50% and about 80% by weight water;

at least about 10% by weight carbohydrate; and a member selected from the group consisting of:

at least about 5% by weight protein, at least about 7% by weight amino acids, amino acid precursors, amino acid analogs, or a combination thereof, a combination of at least about 5% by weight protein and at least about 5% by weight amino acids, amino acid precursors, amino acid analogs, or a combination thereof, a combination of at least about 10% by weight protein, amino acids, amino acid precursors, and amino acid analogs, and at least about 10% by weight protein.

The ratio of carbohydrates to the various nitrogen-containing members in these high moisture materials can be in the range between about 1:1 and about 3:1.

When the high moisture material contains at least about 7% by weight amino acids, amino acid precursors, amino acid analogs, or a combination thereof, or a combination of at least about 10% by weight protein, amino acids, amino acid precursors, and amino acid analogs, the high moisture material can also contain a starch, a gum, or a combination thereof. The starch can be an unmodified starch or a combination of an unmodified starch and a modified starch. When the starch is an unmodified starch, it can be present in an amount of at least about 10% by weight. When the starch is a combination of an unmodified starch and a modified starch, the modified starch can be present in an amount of at least about 0.01% by weight. When a gum is employed, it can be present in an amount of from about 0.001% to about 5% by weight.

To enable hatchlings to more effectively utilize any fats which may be present in the high moisture material or to enable the hatchlings to more effectively utilize its yolk-based lipid and protein, the high moisture material may contain bile salts, cholesterol, surfactants, emulsifying agents, micelles, or an enzyme such as lipase, amylase, maltase, pepsin, trypsin, or other enzyme which commonly occur in the gastrointestinal system, or an enzyme such as keratinase which is not typically found in the gastrointestinal system but which has useful activities. The concentration of the digestion aid will depend upon the application but, in general, will be between about 0.01% and about 5% by weight of the dry matter.

The high moisture material may additionally contain vitamins and minerals. Vitamin additives may be selected, for example, from vitamin A, B12, biotin, choline, folacin, niacin, pantothenic acid, pyridoxine, riboflavin, thiamin, C, D, 25-hydroxy D, E, and K. Mineral additives may be selected, for example, from calcium, phosphorous, selenium, chlorine, magnesium, potassium, sodium, copper, iodine, iron, manganese and chromium pincolinate. The concentration of the vitamins and minerals will depend upon the application but, in general, will be between about 0.01% and about 5% by weight of the dry matter.

Bacterial, yeast or mold preparations, commonly referred to as probiotics or direct fed microbials, have been administered orally or added to animal feeds to provide various benefits such as altering the gastrointestinal microflora/microbiota of poultry and other animals. Those microbial additives which have been approved for use are identified in the annual Feed Additive Compendium published by The Miller Publishing Company (Minnetonka, Minn.) in cooperation with The Animal Health Institute and the Direct-fed Microbial, Enzyme and Forage Additive Compendium published by The Miller Publishing Company. Among the direct-fed microbials which have been approved are strains of the lactic acid bacteria, particularly those classified in the following genera: Lactobacillus, Lactococcus, and Enterococcus. Included among these are the following species: *Lactobacillus reuteri, Lactobacillus acidophilus, Lactobacillus bulgaricus, Lactobacillus plantarum, Lactobacillus casei, Lactobacillus lactis, Lactococcus lactis, Lactococcus thermophilus, Lactococcus diacetylactis,* and *Enterococcus faecium*. In addition to these lactic acid bacteria, some species of Bacillus (such as *Bacillus subtilis* and *Bacillus toyoi*), some species of Streptococcus (such as *Streptococcus faecium*), and yeasts and molds (such as *Saccharomvces cerevisiae, Aspergillus oryzae,* and Torulopsis sp.) have also been used as direct fed microbials.

The high moisture material of the present invention, therefore, may be used as a vehicle to administer direct-fed microbials to poultry and other animals. When used for this purpose, the high moisture material should contain sufficient colony forming units of the yeast or bacterium to be of benefit to the animal. In general, the high moisture material used as a direct fed microbial should contain at least about $10^2$, preferably about $10^4$, and more preferably about $10^6$ colony forming units of bacteria or at least about 10, preferably about $10^2$, and more preferably about $10^4$ colony forming units of yeast per gram of composition. The yeast or bacterium may be incorporated into the high moisture material prior to solidification or it may be deposited on or in the high moisture material after it has solidified. Although the high moisture material may be fed at anytime to alter the gastrointestinal microflora/microbiota of or provide other benefits to the animal, it is preferably fed to poultry as soon as possible after hatching to establish the direct fed microorganism(s) as the dominant flora or culture in the gastrointestinal tract and thereby exclude potential pathogens.

The high moisture material may additionally be used as a vehicle to deliver a variety of other substances to poultry and other animals. For example, the high moisture material may contain a peptide such as epidermal growth factor, transforming growth factor, granulocyte-macrophage colony stimulating factor, erythropoietin, bombesin, fibroblast growth factor, keratinocyte growth factor, nerve growth factor, vascular endothelial growth factor, bovine or other somatotropin or insulin-like growth factor (IGF-I or IGF-II). The high moisture material may also contain a steroid or polypeptide hormone such as, estrogen, glucocorticoids, insulin, glucagon, gastrin, calcitonin or somatotropin. The high moisture material may further contain an antibiotic approved for use in animal feed such as bacitracin, BMD (bacitracin methylenedisalicylate), lincomycin, or virginiamycin or other therapeutic drug. The high moisture material may also additionally contain a natural or synthetic antioxidant such as ethoxyquin, tocopherol, BHT (butylated hydroxytoluene), BHA (butylated hydroxyanisole), vitamin C or glutathione; a receptor, transfer factor, chelator or complexing agent which modifies release rates of nutrients or other bioactive compounds; an immunoactive agent such as cytokines, vaccines and other immunomodulators, immunoglobulins, antigens, killed cells, attenuated strains, toxins, adjuvants or vaccines; or a palatability modifier such as food coloring, grit, oyster shell, whole seeds or grains. The concentration of these additives will depend upon the application but, in general, will be between about 0.1% and about 10% by weight of the dry matter.

A formulation satisfying the nutrient specifications of the high moisture material of the present invention may be prepared, for example, from the following ingredient mix (based upon the weight of the non-aqueous fraction of the high moisture material):

| | |
|---|---|
| soybean meal | 58% |
| dried egg white | 8% |
| corn starch | 4% |
| corn meal | 30% |
| Alimet ® | 0.5% |
| propionic acid | 0.5% |
| citric acid | to pH 3.5–4 |

High moisture materials containing these ingredients (and optionally one or more of the other additives described herein) can be made by dry mixing the ingredients, adding hot water (80° C.) and quickly mixing the wetted ingredients while maintaining the temperature above the starch gelation temperature for at least one minute. The mixture is then stirred and pressed into a dish, cylinder, mold, or other vessel or container.

Although a high moisture material may be prepared from a poultry starter diet formulation, such simple mixtures readily allow the escape of free water which is potentially deleterious. Not only could the hatchling chicks suffer from evaporative cooling as a result of being wetted by the released moisture, they could suffer from consuming high moisture material which contains insufficient moisture. In addition, a loss of moisture could cause a substantial change in the texture of the high moisture material, changing it from a material which the hatchling chicks can break apart by pecking and consume to one which is hard or "leathery" and inaccessible to the birds. It is preferred, therefore, that the high moisture material have an initial moisture content of at least about 40% by weight water and that the high moisture material retain substantially all of its water under the conditions at which it is being provided to the chicks. More preferably, the high moisture material will retain at least 80% and most preferably at least about 90% of its water content when exposed to a temperature of 80° C. and a relative humidity of 70% for 24 hours. To improve the water-retention capability of the high moisture material, humectants, gums, proteins or other ingredients may be included in the formulation.

Similarly, the digestibility of ingredients could be improved with additions to the formulation such as, but not limited to, enzymes, bile salts or surfactants. Similarly, overall performance may be improved with the addition of selected micro ingredients, minerals, microorganisms, growth promotants, hormones, prostaglandins such as $E_2$ or other factors which promote enhanced digestive enzyme activity, nutrient absorption or maturation of the gastrointestinal system as a whole.

In general, highly available protein sources might include hydrolyzed poultry protein, hydrolyzed casein, or peptone. In contrast, less available protein sources such as by-product meals or vegetable proteins might be fed in combination with factors such as proteases or microorganisms that secrete proteases to increase digestibility. Similarly, carbohydrates such as glucose may be chosen for high availability, or more complex sources such as ground corn or potato starch may be supplemented with enzymes or subjected to gelation to increase their availability. Digestibility of saturated fats could be improved through the addition of lipase, bile salts or surfactants. Thus, the formulation would include either highly available ingredients or additives or handling methods which improve digestion of less available ingredients in very young birds. The ingredients would be administered in a semi-solid or solid form.

In addition, it has been demonstrated that the gastrointestinal system of young birds is not able to use certain ingredients such as tallow with the same efficiency as mature birds (Fredde et al., *Factors Affecting the Absorbability of Certain Dietary Fats in the Chick,* J. Nutrition, Vol. 70, pp. 447–452 (1960); Gomez et al., *The Use of Bile Salts to Improve Absorption of Tallow in Chicks, One to Three Weeks of Age,* Poultry Science Vol. 55, pp. 2189–2195 (1976); Polin et al., *The Effect of Bile Acids and Lipase on Absorption of Tallow in Young Chicks,* Poultry Science, Vol. 59, pp. 2738–2743 (1980); Sell et al., *Influence of Age on Utilization of Supplemental Fats by Young Turkeys,* Poultry Science, Vol. 65, pp. 546–554 (1986)). Ontogenetic changes which accompany improved digestion include increased levels of pancreatic and intestinal enzymes (Krogdahl et al., *Influence of Age on Lipase, Amylase, and Protease Activities in Pancreatic Tissue and Intestinal Contents of Young Turkeys,* Poultry Science, Vol. 68, pp. 1561–1568 (1989); Sell et al., *Intestinal Disaccharidases of Young Turkeys: Temporal Development and Influence of Diet Composition,* Poultry Science, Vol. 68, pp. 265–277 (1989); Noy et al., *Digestion and Absorption in the Young Chick,* Poultry Science, Vol. 74, pp. 366–373 (1995)), overall gut surface area for absorption (Nitsan et al., *Growth and Development of the Digestive Organs and Some Enzymes in Broiler Chicks After Hatching,* British Poultry Science, Vol. 32, pp. 515–523 (1991); Nitsan et al., *Organ Growth and Digestive Enzyme Levels to Fifteen Days of Age in Lines of Chickens Differing in Body Weight,* Poultry Science, Vol. 70, pp. 2040–2048 (1991); Sell et al., *Developmental Patterns of Selected Characteristics of the Gastrointestinal Tract of Young Turkeys,* Poultry Science, Vol. 70, pp. 1200–1205 (1991)), and changes in nutrient transporters (Shehata et al., *Development of Brush-Border Membrane Hexose Transport System in Chick Jejunum,* Am. J. Physiol, Vol. 240, pp. G102–G108 (1981); Buddington et al., *Ontogenetic Development of Intestinal Nutrient Transporters,* Annu. Rev.

Physiol., Vol. 51, pp. 601–619 (1989); Moreto et al., *Transport of L-Proline and α-Methyl-D-Glucoside by Chicken Proximal Cecum During Development*, Am. J. Physiol, Vol. 260, pp. G457–G463 (1991)). The high moisture material of the present invention would minimize or exclude poorly used ingredients and substitute more highly available ingredients as assessed by subsequent bird performance.

The quantity of the high moisture material fed will be a function of the animal species, age, environmental conditions such as temperature and humidity and, in the case of poultry, the length of the preplacement period, i.e, the total time consumed in the post-hatch holding period, the processing period and in transit to the poultry production farm. In general, however, at least about 5 grams of high moisture material per chick per day should be provided to 0 to 2 day old chicks, about 10 grams of high moisture material per chick per day should be provided to 2 to 3 day old chicks, and up to about 20 grams of high moisture material per chick per day should be provided to 4 to 7 day old chicks.

As previously noted, chicks conventionally are placed with poultry production farms within about 2 days of hatching. This practice has developed, in part, out of the fact that hatchers typically do not provide food or water to the hatchlings and the fact that the hatchlings must receive water and a source of nutrition by about 3 days or else they suffer. Because the composition of the high moisture materials of the present invention can be controlled to meet the changing nutritional requirements of the hatchlings as they mature, it may become practical for hatchers to delay sending chicks to poultry production farms for a longer period of time or to ship chicks a greater distance without experiencing many of the difficulties associated with providing water and nutrition to the chicks. Thus, for example, hatchers could conveniently feed the high moisture material of the present invention to the chicks for a period of about 3 to about 7 days from hatching before shipping them on to the poultry production farms. Alternatively, the chicks could be shipped from the hatcher to an intermediate facility where they could be fed the high moisture material for a period of about 7 days and then shipped to the standard poultry production farm. Either approach would allow the poultry production farms to more efficiently utilize their houses without burdening the hatchers with feeding the hatchlings water and dry food.

The following examples will illustrate the invention.

EXAMPLE 1

The performance of 1 to 4 day old birds, i.e., birds which were no less than 1 day old and no more than 4 days old at the start of the test as measured from hatching for each bird, fed high moisture solids consisting of agar (1.5% agar and 98.5% by weight water) or agar and egg yolk (1.5% agar, 10% egg yolk and 88.5% by weight water) were compared to fasted and water deprived birds. The results are presented in Table 1. Birds initially lost weight on all feeding regimes and agar alone gave no benefit in either cumulative gain or cumulative feed-to-gain ratio ("FTG"). Agar plus yolk showed an effect on cumulative gain on days 6 and 13, but cumulative feed-to-gain ratio (sometimes referred to herein as cumulative feed efficiency) was poorer than for fasted birds. The data also suggest that hydration alone (agar treatment) with or without yolk conferred no cumulative feed efficiency benefit in this study. Cumulative livability was improved by feeding either water-containing formulation.

TABLE 1

Growth of Birds Fed Nothing or Formulations Consisting of Agar (1.5%) with and without Egg Yolk (10%)

| Trt | Cumul. Gain Day 3 | Cumul. Gain Day 6 | Cumul. FTG Day 6 | Cumul. Gain Day 13 | Cumul. FTG Day 13 | Cumulative Feed Intake Day 13 | Cumulative Livability Day 13 |
|---|---|---|---|---|---|---|---|
| Fasted 24 h | −8.0 | 35.8 g | 1.66 | 1.95.5 g | 1.40 | 274 g | 94% |
| Agar | −7.2 | 32.8 g | 1.95 | 193.7 g | 1.41 | 273 g | 100% |
| Agar & Yolk | −7.8 | 37.5 g | 1.70 | 197.4 g | 1.43 | 282 g | 100% |

EXAMPLE 2

In this example, groups of one to four day old birds were fed for 24 or 48 hours a high moisture solid consisting of starter feed and water. Pens were given enough high moisture solid for each bird to consume 10 g. The feed was present at either 25, 50 or 100% of the high moisture solid. From Table 2 it appears that the high moisture solid containing 25% dry matter gave the best cumulative gain after feeding either 24 or 48 hr. It should be noted, however, that all high moisture solids showed cumulative gain superior to the fasted controls. When cumulative feed efficiency, was corrected for differences in body weight (BW FTG), the 25% dry matter high moisture solid again was superior to the others whether fed for 24 or 48 hr. Cumulative feed intake subsequent to the 48 hr treatment period was higher when birds were given high moisture solids than when they were fasted. This was the case for formulations containing 25, 50 or 100% dry matter. Cumulative livability data suggest that the high moisture solids containing a greater percentage of dry matter are associated with lower livability than the fasted control or 25% dry matter formulations.

TABLE 2

Growth of Birds Fed Starter Feed and Moisture Combinations

| Treatment | Cumul. Gain Day 13 | Cumul. FTG Day 13 | BW Cumul. FTG Day 13 | Cumul. intake Day 13 | Cumulative Livability Day 13 |
|---|---|---|---|---|---|
| Fasted 24 h | 280.9 g | 1.316 | 1.292 | 369.8 g | 100% |
| Formulation 24 h Dry Matter 25% | 303.5 g | 1.319 | 1.285 | 400.3 g | 100% |
| Formation 24 h Dry Matter 50% | 269.0 g | 1.342 | 1.323 | 360.8 g | 100% |
| Formation 24 h Dry Matter 100% | 286.7 g | 1.312 | 1.285 | 375.8 g | 94% |

TABLE 2-continued

Growth of Birds Fed Starter Feed and Moisture Combinations

| Treatment | Cumul. Gain Day 13 | Cumul. FTG Day 13 | BW Cumul. FTG Day 13 | Cumul. intake Day 13 | Cumulative Livability Day 13 |
|---|---|---|---|---|---|
| Fasted 48 h | 222.8 g | 1.371 | 1.372 | 304.6 g | 96% |
| Formation 48 h Dry Matter 25% | 284.6 g | 1.274 | 1.248 | 362.5 g | 100% |
| Formation 48 h Dry Matter 50% | 267.0 g | 1.353 | 1.335 | 360.4 g | 83% |
| Formation 48 h Dry Matter 100% | 237.9 g | 1.394 | 1.389 | 328.4 g | 83% |

EXAMPLE 3

In this example, groups of one to four day old birds were given 20 g each of a high moisture solid consisting of gelatin and Alimet® (2-hydroxy-4-(methylthio)butanoic acid) base with additions of either corn starch or corn starch and lysine. The dry matter content of the high moisture solid was about 5% and the amount of each of the dry matter constituents, based upon the weight of the high moisture solid for each formulation, was as indicated in Table 3. The formulation containing corn starch, gelatin and Alimet® showed cumulative gain and livability superior to the fasted control and the other two formulations. Treatments 2 and 3 also showed superior cumulative feed intake when compared with the fasted control, but the formulations tended to liquify at the brooding temperature and could cause problems in brooding and transit boxes.

EXAMPLE 4

Groups of one to four day old birds were fed formulations containing sources of fats and protein administered with and without added lipase to assist in the digestion of the fat. All formulations contained corn starch, Alimet, lysine and the bile salt, chenodeoxycholic acid. In one case, protein and fat were provided together in the form of yolk solids. In the second case, poultry protein and soy oil were used to provide the protein and fat. The dry matter content of the high moisture solid was about 25% and the amount of each of the dry matter constituents, based upon the weight of the high moisture solid for each formulation, was as indicated in Table 4. Table 4 indicates that the improved cumulative gains and cumulative feed efficiencies were observed in all formulation treatments. Lipase did not appear to be enhance the availability of these complex fat sources. Superior early cumulative feed intake was achieved with yolk solids in the absence of additional lipase. It should be noted that yolk was also used in Example 1, but bird response was not evident in the absence of a source of carbohydrates, bile salts, a methionine source and added lysine.

TABLE 3

Growth of Birds Fed Formulations Containing Starch, Gelatin, Alimet and Lysine Combinations

| Trt | Corn Starch | Gelatin | Alimet ® | Lysine | Cumul Gain Day 14 | Cumul FTG Day 14 | Cumul Intake Day 14 | Cumulative Livability Day 14 |
|---|---|---|---|---|---|---|---|---|
| Fasted 24 hr | | | | | 297.8 g | 1.22 | 358 g | 95% |
| 1 | 0g | 2.5% | .13% | 0 | 290.8 g | 1.32 | 340 g | 80% |
| 2 | 2.5% | 2.5% | .13% | 0 | 317.7 g | 1.23 | 392 g | 100% |
| 3 | 2.5% | 2.5% | .13% | .13% | 289.1 g | 1.34 | 360 g | 80% |

TABLE 4

Growth of Birds Fed Formulations Containing Sources of Protein and Fat, with and without Lipase
(Corn starch: 2.5%, Alimet: .05%, Lysine .05%, Chenodeoxycholic acid: .02%)

| Trt | Addition | Fat | Protein | Cumul. Gain Day 12 | FTG Day 12 | Cumul. intake Day 12 | Cumulative Livability Day 12 |
|---|---|---|---|---|---|---|---|
| Fasted | | | | 253.6 g | 1.30 | 329.2 g | 100% |
| 1 | Egg Yolk (11%) | 7.7% | 3.3% | 284.4 g | 1.22 | 345.6 g | 100% |
| 2 | Lipase (2%) Egg Yolk | 7.7% | 3.3% | 254.0 g | 1.24 | 312.2 g | 100% |

TABLE 4-continued

Growth of Birds Fed Formulations Containing Sources
of Protein and Fat, with and without Lipase
(Corn starch: 2.5%, Alimet: .05%, Lysine .05%, Chenodeoxycholic acid: .02%)

| Trt | Addition | Fat | Protein | Cumul. Gain Day 12 | FTG Day 12 | Cumul. intake Day 12 | Cumulative Livability Day 12 |
|---|---|---|---|---|---|---|---|
| 3 | (11%) Soy Oil (10%) Poultry Protein (10%) | 10% | 7.5% | 264.3 g | 1.25 | 331.2 g | 95% |
| 4 | Lipase (2%) Soy Oil (10%) Poultry Protein (10%) | 10% | 7.5% | 257.9 g | 1.26 | 312.4 g | 100% |

EXAMPLE 5

Groups of one to four day old birds fed agar (1.5% agar and 98.5% water) and agar plus a direct fed microbial (1.5% agar, 88.5% water, 10% Biomate direct fed microbial including the microbial carrier) were compared to a fasted control. The direct fed microbial ("DFM") consisted of two species of Lactobacilli and two species of Bacilli. The direct fed microbial contained $2.2 \times 10^8$ colony forming units per gram of material for each of the Lactobacilli species and $5.5 \times 10^8$ colony forming units per gram of material for each of the Bacilli species with each pen of 8 birds receiving 1 gram of product. Although the cumulative feed efficiency of this treatment was poorer than that of agar alone, cumulative gain appeared to increase in the presence of water and the DFM. The DFM, therefore, provided some benefit on its own and to optimize this effect more nutrients should be added to the high moisture solid.

TABLE 5

Growth of Birds Fed Agar (1.5%) and Agar
Containing a Direct Fed Microbial Consisting of
Lactobacillus acidophilus and lactis, and Bacillus
subtilis and licheniformis (10%)

| Treatment | Cumulative Gain Day 21 | Cumulative Feed to Gain Day 21 | Cumulative Feed Intake Day 21 | Cumulative Livability Day 21 |
|---|---|---|---|---|
| Fasted 24 h | 710.3 g | 1.388 | 985.8 g | 98% |
| Agar (1.5%) | 720.5 g | 1.386 | 998.0 g | 98% |
| Agar (1.5%) DFM (10%) | 724.2 g | 1.387 | 1004.4 g | 98% |

EXAMPLE 6

This example shows the response of one to four day old hatchlings to casein, enzyme hydrolyzed casein and casein administered with a source of proteolytic activity. The high moisture solid contained 85% water with a balance of constituents as indicated in Table 6. In treatment 3, 0.6% pepsin (based upon the weight of the high moisture solid) was added to the formulation and in treatment 4, a microbe which secretes a proteolytic enzyme was added. All formulation treatments showed superior cumulative gain, cumulative feed efficiency and livability when compared to the fasted control.

TABLE 6

Growth of Birds Fed Formulations with Casein, Hydrolyzed Casein, Casein
with Pepsin or Casein with B. licheniformis ($2 \times 10^6$/bird)
(Ground corn: 10%, Agar: 25%, Alimet: .125%, Lysine: .04)

| Trt | Casein | Cumulative Gain Day 12 | Cumulative Feed to Gain Day 12 | Cumulative Feed Intake Day 12 | Cumulative Livability Day 12 |
|---|---|---|---|---|---|
| Fasted 24 h | | 207.2 g | 1.34 | 303.4 g | 79% |
| 1 | Casein (10%) | 249.3 g | 1.21 | 301.7 g | 92% |
| 2 | Hydrolyzed Casein (10%) | 234.8 g | 1.19 | 280.1 g | 96% |
| 3 | Casein (10%) Pepsin (.6%) | 234.8 g | 1.26 | 293.7 g | 91% |

TABLE 6-continued

Growth of Birds Fed Formulations with Casein, Hydrolyzed Casein, Casein
with Pepsin or Casein with B. licheniformis (2 × 10⁶/bird)
(Ground corn: 10%, Agar: 25%, Alimet: .125%, Lysine: .04)

| Trt | Casein | Cumulative Gain Day 12 | Cumulative Feed to Gain Day 12 | Cumulative Feed Intake Day 12 | Cumulative Livability Day 12 |
|---|---|---|---|---|---|
| 4 | Casein (10%) B. licheniformis | 248.8 g | 1.19 | 296.0 g | 91% |

EXAMPLE 7

In this example, zero to two day old birds were fed formulations consisting of 10% dry matter in the form of corn starch (2.5%), protein (5%), and glucose (2.5%), based upon the weight of the high moisture solid. Birds were treated for 24, 48 or 72 hours, to test the possibility of treating birds over the total preplacement period of approximately 2 days in the hatching incubator and 1 day in transit. All formulation treated birds showed cumulative gain superior to birds fasted for an equivalent period. In addition, the birds treated with formulation for 24 and 48 hours also showed superior cumulative feed efficiencies. The response appeared to decline at the 72 hour time point. It appears from these data that 10% dry matter is sufficient to improve performance of young birds over a 2 day period, but that a higher concentration of nutrients may be required by the third day. It should be noted that for each time period, livability of formulation fed birds was superior to fasted controls.

TABLE 7

Growth of Birds Fed Hatchery Formulations Consisting of
Corn Starch (2.5%), Porcine Plasma (5%), Agar (.5%),
Alimet (.125%), Lysine (.125%), Glucose 2.5%; Total 10%
Dry Matter)

| Treatment | Cumulative Gain Day 16 | Cumulative Feed to Gain Day 16 | Cumulative Feed Intake Day 16 | Cumulative Livability Day 16 |
|---|---|---|---|---|
| Fasted 24 h | 405.4 g | 1.431 | 580.1 g | 93% |
| Formulation 24 h | 435.6 g | 1.422 | 619.4 g | 96% |
| Fasted 48 h | 369.3 g | 1.425 | 526.3 g | 95% |
| Formulation 48 h | 391.7 g | 1.413 | 553.5 g | 100% |
| Fasted 72 h | 331.1 g | 1.430 | 473.5 g | 91% |
| Formulation 72 h | 348.6 g | 1.456 | 507.6 g | 93% |

EXAMPLE 8

In this example, the growth of chicks fed nothing, formulations solidified with dehydrated egg white, whole egg or guar/xanthan gums, or a simple gruel of rice and corn was compared. Table 8 shows early bird performance as influenced by formulations solidified in various ways.

Treatment 1 was the fasted control. The formulation in treatments 2 and 3 consisted of corn meal (15%), corn starch (2%), soybean meal (12%) and either dehydrated egg white (3.6%) or whole egg (20%). Treatment 4 had slightly more soybean meal (16%) to compensate for the loss of the egg protein and was solidified with a combination of guar (0.35%) and xanthan (0.05%) gums. Treatment 5 was a simple gruel of rice (22.5%) and corn (22.5%). All formulations contained fumaric (1%) and propionic (0.5%) and a vitamin (0.1%) and mineral (0.05%) premix.

One to four day old birds were weighed (Table 8, body weight day 0) and treated with 10 gm/bird of a high moisture solid or fasted for 24 hours. The birds receiving high moisture solid received one of four high moisture solids designated in Table 8. Birds were then weighed again (body weight day 1) and all were offered water and starter feed for ad libitum consumption. As can be seen in Table 8, fasted birds initially lost weight while formulation treated birds either maintained or even gained weight. Day 6 performance, however, indicated that the higher protein formulations (2–4) were more beneficial than the simple rice and corn mixture. Both body weights and feed efficiencies of birds in treatments 2–4 were superior to those of treatment 5. All birds showed an improvement in early livability compared to fasted controls.

TABLE 8

Growth of Birda Fed Nothing or Formulations
Solidified with Dehydrated Egg White, Whole Egg
or Guar/Xanthan Gums, in Comparison to a Simple
Gruel of Rice and Corn.

| Trt | Treatment Description | Body Weight Day 0 | Body Weight Day 1 | Body Weight Day 6 | Feed to Gain Day 6 | Livability Day 6 |
|---|---|---|---|---|---|---|
| 1 | Fasted Control | 43.5 | 41.8 | 140.9 | 1.305 | 69% |
| 2 | Dehydrated Egg White | 43.4 | 44.8 | 154.9 | 1.121 | 98% |
| 3 | Whole Egg | 43.6 | 45.8 | 156.1 | 1.175 | 98% |
| 4 | Guar and Xanthan Gum | 43.1 | 43.4 | 155.6 | 1.167 | 98% |
| 5 | Rice and Ground Corn | 43.9 | 45.1 | 147.6 | 1.200 | 100% |

EXAMPLE 9

In this example, the water retention characteristics of the various formulations described in Example 8 was compared to that in a simple ground corn and rice gruel. After 24 hours, formulations in which egg or gums were added to bind the water held more moisture than did the simple hot water slurry of rice and ground corn. When these were fed to one to four day old chicks, birds eating the rice and ground corn gruel were noted to be damp, although no measurable water escaped from any of the mixtures. The results are presented in Table 9.

TABLE 9

Water Retention (%) in Formulations after 24 hours at 80, 90 or 100C. and 40% Humidity

| | Water Remaining in Formulation After 24 Hours | | | | | |
|---|---|---|---|---|---|---|
| | 80C. | | 90C. | | 100C. | |
| Formulation | % | g/kg | % | g/kg | % | g/kg |
| Dehydrated Egg White | 26.5 | 175 | 15.5 | 102 | 16.5 | 109 |
| Whole Egg | 26.0 | 172 | 22.5 | 149 | 15.5 | 102 |
| Guar Xanthan Gum | 24.0 | 166 | 22.5 | 156 | 17.0 | 118 |
| Rice and Ground Corn | 14.5 | 80 | 2.8 | 15 | 0 | 0 |

EXAMPLE 9a

Table 9a shows water loss by high moisture solids kept at 80° C. and 70% humidity. Formulations 1–4 contained guar and xanthan gums (0.6–1%), 20–22% soybean meal and about 16% corn meal, with the balance as water. Humectant levels ranged from 1 g (modified corn starch) to 50 g (propylene glycol and glycerol). Formulations 5 and 6 were included as examples of simple formulations which did not include a humectant. Formulation 5 consisted of 21% soybean meal, 11% oats and 8.5% rice, with the balance as water. Prior to the experiment shown in Table 9a, all formulations were kept at room temperature overnight to allow the mixtures to absorb the water. In the absence of a humectant, a gum based gel lost 19% of its water in 24 hours and 34% after 48 hours. High moisture solids containing the humectants propylene glycol and glycerol lost 0–10% of their water in 24 hours and 4–17% after 48 hours. The modified corn starch did not perform as well under these conditions as did the other humectants. Simple mixtures of grain and rice retained the least water under these conditions, losing 24% water over the first 24 hours and 47–53% of their water by 48 hours.

TABLE 9a

Water Retention (80C., 70% Humidity) at 24 and 48 hour by High Moisture Solids Containing Gums or Humectants in Comparison to Simple Mixtures of Grains, Soybean Meal and Rice

| Trt | Formulation Contents | Other | Loss at 24 h (%) | Loss at 48 h (%) |
|---|---|---|---|---|
| 1 | Soybean Meal, Corn Meal & Gum | | 19% | 33% |
| 2 | Soybean Meal, Corn Meal & Gum | Modified Corn Starch | 20% | 42% |
| 3 | Soybean Meal, Corn Meal & Gum | Propylene Glycol | 0% | 4% |
| 4 | Soybean Meal, Corn Meal & Gum | Glycerol | 10% | 17% |
| 5 | Soybean Meal, Rice & Oats | None | 24% | 47% |
| 6 | Ground Corn & Rice | None | 24% | 53% |

EXAMPLE 10

In this example, samples from formulations containing soybean meal (12%), corn meal (17%) and either whole egg (20%) or guar/xanthan gum (4%) stabilized with fumaric (1%) and propionic (0.5%) acids were compared to a simple corn (23%) and rice (23%) mixture for microbial growth. All mixtures were stored sealed (except for sampling) at room temperature. Plates were incubated for 3 days at 37° C. in a saturated atmosphere. MacConkey agar was included to evaluate the growth of Gram negative organisms such as E. Coli. From Table 10 it is clear that the rice and corn mixture was not stable and supported high levels of microbial growth when stored at room temperature in a sealed bag. The heating procedure does not destroy bacillus spores, and these would be the source of the colonies seen in the blood agar at day 1 and 2 in the formulation containing guar and xanthan gums. It is clear, however, that bacilli were not multiplying in the formulation itself, because numbers did not increase with time. The organisms present in the rice and corn gruel included Gram negative rods, Gram positive cocci and yeast.

The formulation made with soybean meal (11%), corn meal (15%), corn starch (2%), dehydrated egg white (6%) and stabilized with citric (1%) and propionic (0.5%) acids was also tested for stability to microbial growth. Samples were stored for 9 weeks without showing any indication of microbial growth when tested on blood agar and MacConkey agar. There was no mold growth evident on the samples and no indication of separation of water from the high moisture solid over this period of time.

TABLE 10

Microbial Growth of a 1:1000 Dilution of Formulation

Number of Colonies in 0.1 ml of a 1:1000 Dilution

| | Whole Egg | | Guar & Xanthan Gums | | Rice & Corn Gruel | |
|---|---|---|---|---|---|---|
| Day | Blood Agar | MacConkey | Blood Agar | MacConkey | Blood Agar | MacConkey |
| Day 1 | 0 | 0 | 1 | 0 | 4 | 0 |
| Day 3 | 0 | 0 | 2 | 0 | 1067 | 53 |
| Day 5 | 0 | 0 | 0 | 0 | 1000 | 0 |
| Day 9 | 0 | 0 | 0 | 0 | 1100 | 90 |

EXAMPLE 11

This example shows the proximate analysis of several high moisture solids in comparison to mixtures of rice and various grains with as much water as the combination will hold (excess water poured off). Values for carbohydrates are obtained by difference. Performance studies using live birds have indicated that the optimum protein level in a high moisture solid fed to day old birds is 10–11%. Using dry matter levels of 33%, feeding a level of 10% protein and 20% carbohydrate in a high moisture solid resulted better day 6 gain and feed conversion results (Example 8) than did a rice and corn mixture containing 4% protein and 35% carbohydrate. A protein level of 10% is not possible using a mixture based on a whole grain and rice or whole grain alone, even with 100% dry matter. Even if the grain were relatively high in protein, such as wheat (maximum 15%), protein levels higher than 7–8% would not be possible in a mixture containing 50% water. With a mixture of wheat and water, a protein level of 10.5% would require 70% dry matter. The results are presented in Table 11.

TABLE 11

Proximate Analysis of Formulations of Corn and Soybean Meal and Containing Dehydrated Egg White to Bind the Water in Comparison to Various Rice, Corn and Water Mixtures.

| | Proximate Analysis | | | | |
|---|---|---|---|---|---|
| Formulation | Carbohydrate % | Protein % | Fat % | Ash % | Water % |
| Soy Meal, Corn Meal & Dehydrated Egg White | 19.1 | 10.3 | .7 | 1.0 | 68.4 |
| Soy Meal, Corn Meal & Whole Egg | 20.0 | 9.4 | 2.2 | 1.0 | 66.8 |
| Soy Meal, Corn Meal & Guar/Xanthan Gum | 23.7 | 10.7 | .2 | 1.2 | 63.4 |
| Rice | 33.8 | 3.1 | .8 | .2 | 62.1 |
| Corn | 41.9 | 4.5 | 2.1 | .6 | 50.2 |
| Rice and Corn | 34.6 | 3.9 | 1.3 | .4 | 41.0 |
| Rice and Oats | 25.5 | 4.3 | 1.2 | .5 | 68.5 |
| Oats, Rice, Rye, Wheat, Triticale and Buckwheat | 15.4 | 3.7 | 1.1 | .5 | 74.8 |

EXAMPLE 12

The objective of this experiment was to determine the optimum ratio of fat, protein, and carbohydrate in a formulation with a 25% solids composition. An experimental design was generated to meet the stated objective and it was implemented as a 96 pen, 41 day study. In this study, 1–4 day old chicks were fed the formulation or were fasted for 48 hours. The results are present in FIG. 1. The performance parameter illustrated in FIG. 1 is the estimated feed conversion for a 2 kg broiler at 41 days. A response surface model was made for feed conversion corrected to a constant live weight. It was found that fat had a large negative impact on performance. The birds treated with greater than 5% fat showed losses in live weight and increased feed conversion. The best performance for this 25% dry matter formulation occurred with the protein and carbohydrate treatments where the birds exhibited body weight corrected feed conversions of 1.72–1.73. Mortality was lowest at 21 days for treatments with higher levels of protein, and highest with treatments that contained significant amounts of fat. Data from this experiment indicate that the optimum digestible carbohydrate level is above 8%.

EXAMPLE 13

Early mortality in turkey poults is a particular problem in this industry. It is ascribed to a number of factors, including failure of the birds to ingest feed and water ad libitum due to an excessively long time between hatch and placement. In this experiment, groups of one to four day old turkey poults were fed a 33% dry matter formulation containing less than 1% fat, 9–10% protein, and 22–23% carbohydrates, or were fasted and deprived of water for either 24 or 48 hours. On a percent dry matter basis, the formulation contained 44% corn meal, 6% corn starch, 36% soybean meal, 11% dehydrated egg white, 2% fumaric acid, and 1.5% propionic acid. As a percentage of the total formulation, this equated to 15% corn meal, 2% corn starch, 12% soybean meal, 3.6% dehydrated egg white, 0.7% fumaric acid, and 0.5% propionic acid. Afterwards, the birds were given a conventional feed formulation. As shown in FIG. 2, the performance of birds on this regime showed differences in 7, 14, and 21 day cumulative mortalities: birds fasted for 24 hours showed mortalities greater than those given formulation for 24 hours. This was further accentuated when birds were fasted or given formulation for 48 hours. In the group fasted for 48 hours, early mortality reached almost 20% by day 21, whereas birds given formulation over the same time period showed the least cumulative 21 day mortality in the study, i.e., less than 10%.

In view of the above, it will be seen that the several objects of the invention are achieved.

As various changes could be made in the above compositions and processes without departing from the scope of the invention, it is intended that all matter contained in the above description be interpreted as illustrative and not in a limiting sense.

What is claimed is:

1. A process for enhancing the health, livability, cumulative weight gain, or feed conversion efficiency of poultry, comprising making available to poultry hatchlings for consumption ad libitum a high moisture material before said poultry hatchlings are offered dry food ad libitum, the high moisture material comprising water and a dry matter fraction, wherein said high moisture material contains, on a percent weight basis of the total composition:
at least about 20% water;
about 8.5% to about 18.5% carbohydrate;
about 6.5% to about 15.77% amino acid source; and
0% to about 4.44% fat,
wherein the water retention capacity of said high moisture material is such that it does not release free water in an amount sufficient to dampen said poultry hatchlings as a consequence of their coming into contact with it.

2. The process of claim 1, wherein said high moisture material contains at least about 40% by weight water.

3. The process of claim 1, wherein said high moisture material contains at least about 50% by weight water.

4. The process of claim 1, wherein said high moisture material contains between about 50% and about 85% by weight water.

5. The process of claim 1, wherein said high moisture material contains between about 60% and about 80% by weight water.

6. The process of claim 1, wherein said carbohydrate is selected from the group consisting of corn starch, wheat starch, modified corn starch, a gum, whole, ground, cracked, milled, rolled, extruded, pelleted, defatted, dehydrated, solvent extracted, or other processed form of corn or wheat, and mixtures thereof.

7. The process of claim 6, wherein said gum is selected from the group consisting of agar, algin, carrageenan, gum arabic, gum ghatti, gum tragacanth, guar gum, locust bean gum, and pectin.

8. The process of claim 1, wherein said amino acid source is selected from the group consisting of methionine, tryptophan, threonine, arginine, lysine, 2-hydroxy-4-(methylthio)butanoic acid, a salt of 2-hydroxy-4-(methylthio)butanoic acid, serum proteins, casein, soybean meal, fishmeal, meat meal, egg white, egg yolk, eggs without shells, and mixtures thereof.

9. The process of claim 1, wherein said fat is an isolated plant oil.

10. The process of claim 1, wherein:
said carbohydrate is selected from the group consisting of corn starch, wheat starch, modified corn starch, a gum, whole, ground, cracked, milled, rolled, extruded, pelleted, defatted, dehydrated, solvent extracted, or other processed form of corn or wheat, and mixtures thereof;
said amino acid source is selected from the group consisting of methionine, tryptophan, threonine, arginine, lysine, 2-hydroxy-4-(methylthio)butanoic acid, a salt of 2-hydroxy-4-(methylthio)butanoic acid, serum proteins, casein, soybean meal, fishmeal, meat meal, egg white, egg yolk, eggs without shells, and mixtures thereof; and
said fat is an isolated plant oil.

11. The process of claim 10, wherein said high moisture material contains between about 60% and about 80% by weight water.

12. The process of claim 1, wherein the weight ratio of all digestible carbohydrate to all amino acid sources in said high moisture material is between about 0.6:1 and about 3:1, respectively.

13. The process of claim 11, wherein the weight ratio of all digestible carbohydrate to all amino acid sources in said high moisture material is between about 0.6:1 and about 3:1, respectively.

14. The process of claim 1, wherein the dry matter fraction of said high moisture material further contains between about 0.1% and about 10% by weight of an additive selected from the group consisting of a vitamin, a mineral, an enzyme co-factor, a growth promoter, a receptor, a transfer factor, a chelator, a complexing agent, a palatability modifier, a digestion aid, a peptide, a hormone, a prostaglandin, a steroid, an antibiotic, an antioxidant, an immunoactive agent, a direct fed microbial, and mixtures thereof.

15. The process of claim 14, wherein said digestion aid is selected from the group consisting of an enzyme, a bile salt, cholesterol, a micelle, a surfactant, and an emulsifying agent.

16. The process of claim 15, wherein said enzyme is selected from the group consisting of a gastrointestinal system enzyme, keratinase, and a mixture thereof.

17. The process of claim 16, wherein said gastrointestinal system enzyme is selected from the group consisting of a lipase, an amylase, a maltase, pepsin, and trypsin.

18. The process of claim 14, wherein said digestion aid is present in an amount between about 0.01% and about 5% by weight of the dry matter fraction of said high moisture material.

19. The process of claim 14, wherein said direct fed microbial is selected from the group consisting of bacteria, yeast, molds, and mixtures thereof.

20. The process of claim 19, wherein said bacteria are members of genera selected from the group consisting of Lactobacillus, Lactococcus, Enterococcus, Bacillus and Streptococcus.

21. The process of claim 20, wherein:
said members of the genus Lactobacillus are selected from the group consisting of *Lactobacillus reuteri, Lactobacillus acidophilus, Lactobacillus bulgaricus, Lactobacillus plantarum, Lactobacillus casei,* and *Lactobacillus lactis;*
said members of the genus Lactococcus are selected from the group consisting of *Lactococcus lactis, Lactococcus thermophilus,* and *Lactococcus diacetylactis;*
said Enterococcus is *Enterococcus faecium;*
said members of the genus Bacillus are selected from the group consisting of *Bacillus subtilis* and *Bacillus toyoi;* and
said Streptococcus is *Streptococcus faecium.*

22. The process of claim 19, wherein said yeast or mold is selected from the group consisting of *Saccharomyces cerevisiae, Aspergillus oryzae,* and Torulopsis spp.

23. The process of claim 19, wherein:
said bacteria are present in an amount of at least about $10^2$ colony forming units per gram of said high moisture material; and
said yeast is present in an amount of at least about 10 colony forming units per gram of said high moisture material.

24. The process of claim 14, wherein:
said immunoactive agent is an immunomodulator;
said peptide is selected from the group consisting of epidermal growth factor, transforming growth factor, granulocyte-macrophage colony stimulating factor, erythropoietin, bombesin, fibroblast growth factor, keratinocyte growth factor, nerve growth factor, vascular endothelial growth factor, and insulin-like growth factor;
said steroid is a glucocorticoid steroid;
said hormone is selected from the group consisting of an estrogen, insulin, glucagon, gastrin, calcitonin, and somatotropin;
said antibiotic is selected from the group consisting of bacitracin, bacitracin methylenedisalicylate, lincomycin, and virginiamycin;
said antioxidant is selected from the group consisting of ethoxyquin, tocopherol, butylated hydroxytoluene, butylated hydroxyanisole, vitamin C, and glutathione; and
said palatability modifier is selected from the group consisting of food coloring, grit, oyster shell, whole seeds, and grains.

25. The process of claim 24, wherein said immunomodulator is selected from the group consisting of a cytokine, a vaccine, an immunoglobulin, an antigen, a killed cell, an attenuated strain, a toxin, and an adjuvant.

26. The process of claim 1, wherein said high moisture material retains substantially all of its water under the conditions in which it is provided to said poultry hatchlings.

27. The process of claim 1, wherein said high moisture material retains at least 80% of its water when exposed to a temperature of 80° C. and a relative humidity of 70% for 24 hours.

28. The process of claim 1, wherein said high moisture material is in the form of an extrudate.

29. The process of claim 1, wherein said making available to said poultry for consumption ad libitum said high moisture material is performed by a process selected from the group consisting of:
placing said high moisture material in an incubator along with poultry eggs, thereby making said high moisture material available to said poultry hatchlings upon hatching;

providing said high moisture material to said poultry hatchlings prior to placing said poultry hatchlings in a container for shipment to a poultry farm;

placing said high moisture material along with said poultry hatchlings in a container for shipment of said poultry hatchlings to a poultry farm; and providing said high moisture material to said poultry hatchlings after they have been shipped from the site where they were hatched to a remote location.

30. The process of claim 1, wherein said making available for consumption ad libitum said high moisture material is performed by placing said high moisture material in an incubator along with poultry eggs, thereby making said high moisture material available to said poultry hatchlings upon hatching.

31. The process of claim 1, wherein said making available for consumption ad libitum said high moisture material is performed by providing said high moisture material to said poultry hatchlings prior to placing said poultry hatchlings in a container for shipment to a poultry farm.

32. The process of claim 1, wherein said making available for consumption ad libitum said high moisture material is performed by placing said high moisture material along with said poultry hatchlings in a container for shipment of said poultry hatchlings to a poultry farm.

33. The process of claim 1, wherein said poultry hatchlings are chicken hatchlings.

34. The process of claim 1, wherein said poultry hatchlings are within seven days after hatching.

35. The process of claim 1, wherein said high moisture material contains, on a percent weight basis of the total composition:
at least about 20% water;
about 11.45% to about 16.45% of said carbohydrate;
about 8.65% to about 13.85% of said amino acid source; and
0% to about 1.67% of said fat.

36. The process of claim 35, wherein:
said carbohydrate is selected from the group consisting of corn starch, wheat starch, modified corn starch, a gum, whole, ground, cracked, milled, rolled, extruded, pelleted, defatted, dehydrated, solvent extracted, or other processed form of corn or wheat, and mixtures thereof;
said amino acid source is selected from the group consisting of methionine, tryptophan, threonine, arginine, lysine, 2-hydroxy-4-(methylthio)butanoic acid, a salt of 2-hydroxy-4-(methylthio)butanoic acid, serum proteins, casein, soybean meal, fishmeal, meat meal, egg white, egg yolk, eggs without shells, and mixtures thereof; and
said fat is an isolated plant oil.

37. The process of claim 36, wherein said gum is selected from the group consisting of agar, algin, carrageenan, gum arabic, gum ghatti, gum tragacanth, guar gum, locust bean gum, and pectin.

38. The process of claim 36, wherein said high moisture material contains between about 60% and about 80% by weight water.

39. The process of claim 38, wherein the weight ratio of all digestible carbohydrate to all amino acid sources in said high moisture material is between about 0.6:1 and about 3:1, respectively.

40. The process of claim 35, wherein the dry matter fraction of said high moisture material further contains between about 0.1% and about 10% by weight of an additive selected from the group consisting of a vitamin, a mineral, an enzyme co-factor, a growth promoter, a receptor, a transfer factor, a chelator, a complexing agent, a palatability modifier, a digestion aid, a peptide, a hormone, a prostaglandin, a steroid, an antibiotic, an antioxidant, an immunoactive agent, a direct fed microbial, and mixtures thereof.

41. The process of claim 35, wherein said high moisture material is in the form of an extrudate.

42. A process for enhancing the health, livability, cumulative weight gain, or feed conversion efficiency of poultry or other animals, comprising making available for consumption ad libitum to poultry hatchlings or other animals a high moisture material comprising water and dry matter,
wherein said high moisture material contains, on a percent weight basis of the total composition:
about 60% to about 80% water;
about 8.5% to about 18.5% carbohydrate comprising corn meal and corn starch; and
about 6.5% to about 15.77% amino acid source comprising soybean meal and egg white or whole eggs without shells,
before said poultry hatchlings or other animals are offered dry food ad libitum.

43. The process of claim 42, wherein said making available for consumption ad libitum to poultry hatchlings said said high moisture material is performed by placing said high moisture material along with said poultry hatchlings in a container for shipment of said poultry hatchlings to a poultry farm.

44. A process for enhancing the health, livability, cumulative weight gain, or feed conversion efficiency of poultry or other animals, comprising making available for consumption ad libitum to poultry hatchlings or other animals a high moisture material comprising water and dry matter,
wherein said high moisture material contains, on a percent weight basis of the total composition:
about 60% to about 80% water;
about 8.5% to about 18.5% carbohydrate comprising corn meal and corn starch; and
about 6.5% to about 15.77% soybean meal,
before said poultry hatchlings or other animals are offered dry food ad libitum.

45. The process of claim 44, wherein said making available for consumption ad libitum to poultry hatchlings said high moisture material is performed by placing said high moisture material along with said poultry hatchlings in a container for shipment of said poultry hatchlings to a poultry farm.

46. A process for enhancing the health, livability, cumulative weight gain, or feed conversion efficiency of poultry or other animals, comprising making available for consumption ad libitum to poultry hatchlings or other animals a high moisture material comprising water and dry matter,
wherein said high moisture material contains, on a percent weight basis of the total composition:
about 60% to about 80% water;
about 8.5% to about 18.5% carbohydrate comprising corn meal and corn starch; and
about 6.5% to about 15.77% amino acid source comprising soybean meal and egg white or whole eggs without shells,
before said poultry hatchlings or other animals are offered dry food ad libitum.

47. The process of claim 46, wherein said making available for consumption ad libitum said high moisture material is performed by placing said high moisture material along with said poultry hatchlings in a container for shipment of said poultry hatchlings to a poultry farm.

48. The process of claim 47, wherein said high moisture material further contains a food coloring and an acid stabilizer.

49. The process of claim 48, wherein said acid stabilizer is selected from the group consisting of citric acid, fumaric acid, propionic acid, and phosphoric acid.

50. The process of claim 44, wherein said high moisture material further contains a food coloring and an acid stabilizer.

51. The process of claim 50, wherein said acid stabilizer is selected from the group consisting of citric acid, fumaric acid, propionic acid, and phosphoric acid.

52. The process of claim 45, wherein said high moisture material further contains a food coloring and an acid stabilizer.

53. The process of claim 52, wherein said acid stabilizer is selected from the group consisting of citric acid, fumaric acid, propionic acid, and phosphoric acid.

54. The process of claim 46, wherein said high moisture material further contains a food coloring and an acid stabilizer.

55. The process of claim 54, wherein said acid stabilizer is selected from the group consisting of citric acid, fumaric acid, propionic acid, and phosphoric acid.

56. A process for enhancing the health, livability, cumulative weight gain, or feed conversion efficiency of poultry, comprising making available to said poultry for consumption ad libitum a high moisture material before said poultry are offered dry food ad libitum, the high moisture material comprising water and a dry matter fraction, wherein said high moisture material contains, on a percent weight basis of the total composition:
at least about 20% water;
about 8.5% to about 18.5% carbohydrate;
about 6.5% to about 15.77% amino acid source; and
0% to about 4.44% fat,
wherein the water retention capacity of said high moisture material is such that it does not release free water in an amount sufficient to dampen poultry hatchlings as a consequence of their coming into contact with it, and
wherein said high moisture material is made available to said poultry for consumption ad libitum by extruding said high moisture material to a location where it can be consumed by said poultry or other animals.

57. The process of claim 56, wherein said high moisture material contains between about 50% and about 85% by weight water.

58. The process of claim 56, wherein said high moisture material contains between about 60% and about 80% by weight water.

59. The process of claim 56, wherein:
said carbohydrate is selected from the group consisting of corn starch, wheat starch, modified corn starch, a gum, whole, ground, cracked, milled, rolled, extruded, pelleted, defatted, dehydrated, solvent extracted, or other processed form of corn or wheat, and mixtures thereof;
said amino acid source is selected from the group consisting of methionine, tryptophan, threonine, arginine, lysine, 2-hydroxy-4-(methylthio)butanoic acid, a salt of 2-hydroxy-4-(methylthio)butanoic acid, serum proteins, casein, soybean meal, fishmeal, meat meal, egg white, egg yolk, eggs without shells, and mixtures thereof; and said fat is an isolated plant oil.

60. The process of claim 56, wherein the dry matter fraction of said high moisture material further contains between about 0.1% and about 10% by weight of an additive selected from the group consisting of a vitamin, a mineral, an enzyme co-factor, a growth promoter, a receptor, a transfer factor, a chelator, a complexing agent, a palatability modifier, a digestion aid, a peptide, a hormone, a prostaglandin, a steroid, an antibiotic, an antioxidant, an immunoactive agent, a direct fed microbial, and mixtures thereof.

61. The process of claim 56, wherein said making available for consumption ad libitum said high moisture material to said poultry is performed by placing said high moisture material along with said poultry hatchlings in a container for shipment of said poultry hatchlings to a poultry farm.

62. A process for enhancing the health, livability, cumulative weight gain, or feed conversion efficiency of poultry or other animals, comprising making available to said poultry for consumption ad libitum a high moisture material before said poultry are offered dry food ad libitum, the high moisture material comprising water and a dry matter fraction, wherein said high moisture material contains between about 30% and about 90% by weight water and between about 10% and about 70% dry matter based upon the weight of said high moisture material,
wherein said dry matter contains between about 10% and about 90% by weight carbohydrate based upon the weight of said dry matter, and
wherein the water retention capacity of said high moisture material is such that it does not release free water in an amount sufficient to dampen poultry hatchlings as a consequence of their coming into contact with it.

63. A process for enhancing the health, livability, cumulative weight gain, or feed conversion efficiency of poultry or other animals, comprising making available to said poultry or other animals for consumption ad libitum a high moisture material containing, on a percent weight basis of the total composition:
67% water;
22 to 23% carbohydrate;
9–10% amino acid source; and
less than 1% fat,
before said poultry or other animals are offered dry food ad libitum,
wherein the water retention capacity of said high moisture material is such that it does not release free water in an amount sufficient to dampen said poultry as a consequence of their coming into contact with it.

64. The process of claim 63, wherein:
said carbohydrate is selected from the group consisting of corn starch, wheat starch, modified corn starch, a gum, whole, ground, cracked, milled, rolled, extruded, pelleted, defatted, dehydrated, solvent extracted, or other processed form of corn or wheat, and mixtures thereof.

65. The process of claim 64, wherein said gum is selected from the group consisting of agar, algin, carrageenan, gum arabic, gum ghatti, gum tragacanth, guar gum, locust bean gum, and pectin.

66. The process of claim 63, wherein:
said amino acid source is selected from the group consisting of methionine, tryptophan, threonine, arginine, lysine, 2-hydroxy-4-(methylthio)butanoic acid, a salt of 2-hydroxy-4-(methylthio)butanoic acid, serum proteins, casein, soybean meal, fishmeal, meat meal, egg white, egg yolk, eggs without shells, and mixtures thereof.

67. The process of claim 63, wherein said fat is an isolated plant oil.

68. The process of claim 63, wherein said high moisture material further contains between about 0.1% and about 10% by weight of an additive selected from the group consisting of a vitamin, a mineral, an enzyme co-factor, a growth promoter, a receptor, a transfer factor, a chelator, a complexing agent, a palatability modifier, a digestion aid, a peptide, a hormone, a prostaglandin, a steroid, an antibiotic, an antioxidant, an immunoactive agent, a direct fed microbial, and mixtures thereof.

69. The process of claim 63, wherein said high moisture material is in the form of an extrudate.

70. The process of claim 63, wherein:
said carbohydrate is a mixture of corn meal and corn starch; and
said amino acid source is a mixture of soybean meal and egg white.

71. The process of claim 63, wherein said poultry are turkey poults.

72. The process of claim 71, wherein said turkey poults are one to four days old.

73. The process of claim 63, wherein said making available to said poultry said high moisture material for consumption ad libitum is performed by a process selected from the group consisting of:
placing said high moisture material in an incubator along with poultry eggs, thereby making said high moisture material available to said poultry upon hatching;
providing said high moisture material to said poultry prior to placing said poultry in a container for shipment to a poultry farm;
placing said high moisture material along with said poultry in a container for shipment of said poultry to a poultry farm; and
providing said high moisture material to said poultry hatchlings after they have been shipped from the site where they were hatched to a remote location.

74. The process of claim 63, wherein said making available to said poultry said high moisture material for consumption ad libitum is performed by placing said high moisture material along with said poultry in a container for shipment of said poultry to a poultry farm.

75. A process for enhancing the health, livability, cumulative weight gain, or feed conversion efficiency of poultry or other animals, comprising making available to said poultry or other animals for consumption ad libitum a high moisture material containing, on a percent weight basis of the total composition:
67% water;
15% corn meal;
2% corn starch;
12% soybean meal; and
3.6% dehydrated egg white,
before the poultry is offered dry food ad libitum,
wherein the water retention capacity of said high moisture material is such that it does not release free water in an amount sufficient to dampen said poultry as a consequence of their coming into contact with it.

76. The process of claim 75, wherein said high moisture material further contains between about 0.1% and about 10% by weight of an additive selected from the group consisting of a vitamin, a mineral, an enzyme co-factor, a growth promoter, a receptor, a transfer factor, a chelator, a complexing agent, a palatability modifier, a digestion aid, a peptide, a hormone, a prostaglandin, a steroid, an antibiotic, an antioxidant, an immunoactive agent, a direct fed microbial, and mixtures thereof.

77. The process of claim 75, wherein said high moisture material is in the form of an extrudate.

78. The process of claim 75, wherein said poultry are turkey poults.

79. The process of claim 78, wherein said turkey poults are one to four days old.

80. The process of claim 75, wherein said making available to said poultry said high moisture material for consumption ad libitum is performed by a process selected from the group consisting of:
placing said high moisture material in an incubator along with poultry eggs, thereby making said high moisture material available to said poultry upon hatching;
providing said high moisture material to said poultry prior to placing said poultry in a container for shipment to a poultry farm;
placing said high moisture material along with said poultry in a container for shipment of said poultry to a poultry farm; and
providing said high moisture material to said poultry hatchlings after they have been shipped from the site where they were hatched to a remote location.

81. The process of claim 80, wherein said making available to said poultry said high moisture material for consumption ad libitum is performed by placing said high moisture material along with said poultry in a container for shipment of said poultry to a poultry farm.

82. A process for enhancing the health, livability, cumulative weight gain, or feed conversion efficiency of poultry or other animals, comprising making available for consumption ad libitum a high moisture material to the poultry or other animals before the poultry or other animals are allowed to eat dry food ad libitum, the high moisture material containing between about 30% and about 90% by weight water and between about 10% and about 70% dry matter based upon the weight of the high moisture material,
wherein the dry matter contains at least about 10% by weight carbohydrate and between about 15% and about 50% by weight of an amino acid source based on the weight of the dry matter, and
wherein the water retention capacity of said high moisture material is such that it does not release free water in an amount sufficient to dampen poultry hatchlings as a consequence of their coming into contact with it.

83. The process of claim 82, wherein:
said carbohydrate is selected from the group consisting of corn starch, wheat starch, modified corn starch, a gum, whole, ground, cracked, milled, rolled, extruded, pelleted, defatted, dehydrated, solvent extracted, or other processed form of corn or wheat, and mixtures thereof; and
said amino acid source is selected from the group consisting of methionine, tryptophan, threonine, arginine, lysine, 2-hydroxy-4-(methylthio)butanoic acid, a salt of 2-hydroxy-4-(methylthio)butanoic acid, serum proteins, casein, soybean meal, fishmeal, meat meal, egg white, egg yolk, eggs without shells, and mixtures thereof.

84. The process of claim 82, wherein:

said carbohydrate is selected from the group consisting of corn starch, wheat starch, modified corn starch, a gum, whole, ground, cracked, milled, rolled, extruded, pelleted, defatted, dehydrated, solvent extracted, or other processed form of corn or wheat, and mixtures thereof; and said amino acid source is selected from the group consisting of serum proteins, plasma, meat meal, casein, milk, blood, whey, bloodmeal, egg offal, egg white, egg yolk, eggs without shells, wheat protein, wheat germ, gluten, hydrolysates of serum proteins, hydrolysates of whey, hydrolysates of blood meal, hydrolysates of blood, hydrolysates of egg offal, hydrolysates of egg white, hydrolysates of egg yolk, hydrolysates of eggs without shells, and mixtures thereof.

85. A process for enhancing the health, livability, cumulative weight gain, or feed conversion efficiency of poultry or other animals, comprising making available to said poultry or other animals for consumption ad libitum a high moisture material before said poultry or other animals are offered dry food ad libitum, the high moisture material comprising water and a dry matter fraction, wherein said high moisture material contains, on a percent weight basis of the total composition:

at least about 20% water;

about 8.5% to about 18.5% carbohydrate selected from the group consisting of corn starch, wheat starch, modified corn starch, a gum, whole, ground, cracked, milled, rolled, extruded, pelleted, defatted, dehydrated, solvent extracted, or other processed form of corn or wheat, and mixtures thereof;

about 6.5% to about 15.77% amino acid source selected from the group consisting of serum proteins, plasma, meat meal, casein, milk, blood, whey, bloodmeal, egg offal, egg white, egg yolk, eggs without shells, wheat protein, wheat germ, gluten, hydrolysates of serum proteins, hydrolysates of whey, hydrolysates of blood proteins, hydrolysates of blood, hydrolysates of egg offal, hydrolysates of egg white, hydrolysates of egg yolk, hydrolysates of eggs without shells, and mixtures thereof; and 0% to about 4.44% fat, wherein the water retention capacity of said high moisture material is such that it does not release free water in an amount sufficient to dampen poultry hatchlings as a consequence of their coming into contact with it.

86. The process of claim 85, wherein said high moisture material contains between about 60% and about 80% by weight water.

87. A process for enhancing the health, livability, cumulative weight gain, or feed conversion efficiency of poultry or other animals, comprising making available for consumption ad libitum to poultry hatchlings or other animals a high moisture material comprising water and dry matter, wherein said high moisture material contains, on a percent weight basis of the total composition:

about 60% to about 80% water;

about 8.5% to about 18.5% carbohydrate comprising corn meal and corn starch;

about 6.5% to about 15.77% soybean meal;

a food coloring; and an acid stabilizer selected from the group consisting of citric acid, fumaric acid, propionic acid, and phosphoric acid, before said poultry hatchlings or other animals are offered dry food ad libitum, wherein said making available for consumption ad libitum to poultry hatchlings said high moisture material is performed by placing said high moisture material along with said poultry hatchlings in a container for shipment of said poultry hatchlings to a poultry farm.

88. A process for enhancing the health, livability, cumulative weight gain, or feed conversion efficiency of poultry or other animals, comprising making available for consumption ad libitum to poultry hatchlings or other animals a high moisture material comprising water and dry matter, wherein said high moisture material contains, on a percent weight basis of the total composition:

about 60% to about 80% water;

about 8.5% to about 18.5% carbohydrate comprising corn meal and corn starch;

about 6.5% to about 15.77% amino acid source comprising soybean meal and egg white or whole eggs without shells;

a food coloring; and an acid stabilizer selected from the group consisting of citric acid, fumaric acid, propionic acid, and phosphoric acid, before said poultry hatchlings or other animals are offered dry food ad libitum, wherein said making available for consumption ad libitum to poultry hatchlings said high moisture material is performed by placing said high moisture material along with said poultry hatchlings in a container for shipment of said poultry hatchlings to a poultry farm.

89. A process for enhancing the health, livability, cumulative weight gain or feed conversion efficiency of poultry, the process comprising making available to poultry hatchlings for consumption *ad libitum* a high moisture material containing at least about 40% by weight water and at least about 8% by weight of a digestible carbohydrate before the poultry is offered dry food *ad libitum*, the high moisture material having a capacity for water-retention which is characterized by the absence of the release of free water from the high moisture material in an amount sufficient to dampen the hatchlings as a consequence of their coming into contact with and consuming it.

90. The process of claim 89 wherein the digestible carbohydrate comprises a complex carbohydrate selected from the group consisting of corn, rice, oats, barley, wheat, sorghum, rye, millet, cassava, triticale and tapioca or an isolated carbohydrate selected from the group consisting of corn, potato, wheat and rice starches.

91. The process of claim 89 wherein the digestible carbohydrate comprises a complex carbohydrate selected from the group consisting of corn and rice, or an isolated carbohydrate selected from the group consisting of corn and rice starches.

92. The process of claim 91 wherein the high moisture material is an extrudate.

93. The process of claim 89 wherein the high moisture material is an extrudate.

94. The process of claim 89 wherein the high moisture material comprises at least about 7% by weight of an amino acid source.

95. The process of claim 94 wherein the digestible carbohydrate comprises a complex carbohydrate selected from the group consisting of corn, rice, oats, barley, wheat, sorghum, rye, millet, cassava, triticale and tapioca or an isolated carbohydrate selected from the group consisting of corn, potato, wheat and rice starches.

96. The process of claim 94 wherein the digestible carbohydrate comprises a complex carbohydrate selected from the group consisting of corn and rice, or an isolated carbohydrate selected from the group consisting of corn and rice starches.

97. The process of claim 94 wherein the high moisture material is an extrudate.

98. The process of claim 94 wherein the amino acid source comprises soybean meal, isolated soybean protein, wheat protein, wheat germ, distillers grains, gluten, milk, blood, whey, blood meal, meatmeal, feathermeal, fishmeal, meat and bone meal, poultry offal, egg offal, egg white, egg yolk or eggs without shells.

99. The process of claim 98 wherein the digestible carbohydrate comprises a complex carbohydrate selected from the group consisting of corn, rice, oats, barley, wheat, sorghum, rye, millet, cassava, triticale and tapioca or an isolated carbohydrate selected from the group consisting of corn, potato, wheat and rice starches.

100. The process of claim 98 wherein the digestible carbohydrate comprises a complex carbohydrate selected from the group consisting of corn and rice, or an isolated carbohydrate selected from the group consisting of corn and rice starches.

101. The process of claim 100 wherein the high moisture material is an extrudate.

102. The process of claim 94 wherein the amino acid source comprises soybean meal, isolated soybean protein, wheat protein, wheat germ, egg white, egg yolk or eggs without shells.

103. The process of claim 102 wherein the digestible carbohydrate comprises a complex carbohydrate selected from the group consisting of corn, rice, oats, barley, wheat, sorghum, rye, millet, cassava, triticale and tapioca or an isolated carbohydrate selected from the group consisting of corn, potato, wheat and rice starches.

104. The process of claim 102 wherein the digestible carbohydrate comprises a complex carbohydrate selected from the group consisting of corn and rice, or an isolated carbohydrate selected from the group consisting of corn and rice starches.

105. The process of claim 104 wherein the high moisture material is an extrudate.

106. The process of claim 89 wherein the high moisture material comprises at least about 20% by weight carbohydrate.

107. The process of claim 106 wherein the digestible carbohydrate comprises a complex carbohydrate selected from the group consisting of corn, rice, oats, barley, wheat, sorghum, rye, millet, cassava, triticale and tapioca or an isolated carbohydrate selected from the group consisting of corn, potato, wheat and rice starches.

108. The process of claim 106 wherein the digestible carbohydrate comprises a complex carbohydrate selected from the group consisting of corn and rice, or an isolated carbohydrate selected from the group consisting of corn and rice starches.

109. The process of claim 106 wherein the high moisture material is an extrudate.

110. The process of claim 106 wherein the high moisture material comprises at least about 7% by weight of an amino acid source.

111. The process of claim 110 wherein the digestible carbohydrate comprises a complex carbohydrate selected from the group consisting of corn, rice, oats, barley, wheat, sorghum, rye, millet, cassava, triticale and tapioca or an isolated carbohydrate selected from the group consisting of corn, potato, wheat and rice starches.

112. The process of claim 111 wherein the digestible carbohydrate comprises a complex carbohydrate selected from the group consisting of corn and rice, or an isolated carbohydrate selected from the group consisting of corn and rice starches.

113. The process of claim 112 wherein the high moisture material is an extrudate.

* * * * *